(12) United States Patent
Li et al.

(10) Patent No.: US 9,724,637 B2
(45) Date of Patent: Aug. 8, 2017

(54) METHOD AND APPARATUS FOR CIRCULATING A GLYCOL STREAM, AND METHOD OF PRODUCING A NATURAL GAS PRODUCT STREAM

(71) Applicant: SHELL OIL COMPANY, Houston, TX (US)

(72) Inventors: Bei Li, Rijswijk (NL); Stephen John Mills, Rijswijk (NL); Johan Jan Barend Pek, Rijswijk (NL)

(73) Assignee: SHELL OIL COMPANY, Houston, TX (US)

( * ) Notice: Subject to any disclaimer, the term of this patent is extended or adjusted under 35 U.S.C. 154(b) by 264 days.

(21) Appl. No.: 14/409,420

(22) PCT Filed: Jun. 20, 2013

(86) PCT No.: PCT/EP2013/062852
§ 371 (c)(1),
(2) Date: Dec. 18, 2014

(87) PCT Pub. No.: WO2013/190030
PCT Pub. Date: Dec. 27, 2013

(65) Prior Publication Data
US 2015/0135954 A1     May 21, 2015

(30) Foreign Application Priority Data

Jun. 22, 2012  (EP) .................................... 12173104
Oct. 8, 2012   (EP) .................................... 12187663

(51) Int. Cl.
*B01D 3/14*    (2006.01)
*B01D 3/32*    (2006.01)
(Continued)

(52) U.S. Cl.
CPC ........... *B01D 53/1425* (2013.01); *B01D 3/14* (2013.01); *B01D 3/32* (2013.01); *B01D 53/18* (2013.01);
(Continued)

(58) Field of Classification Search
CPC .... B01D 2252/2023; B01D 3/14; B01D 3/32; B01D 53/1425; B01D 53/18;
(Continued)

(56) References Cited

U.S. PATENT DOCUMENTS

| 4,005,997 A * | 2/1977 | Fowler ..................... B01D 3/36 95/190 |
| 6,023,003 A | 2/2000 | Dunning et al. |

(Continued)

OTHER PUBLICATIONS

Marion Seiersten et al., "Development of a simulator for ethylene glycol loops based on solution thermodynamics and particle formation kinetics".

(Continued)

*Primary Examiner* — Duane Smith
*Assistant Examiner* — Cabrena Holecek

(57) ABSTRACT

The methods apparatuses described herein involve recovering of glycol from an aqueous phase to form a stream of recovered glycol and a glycol recovery system. The aqueous phase is fed to the top of a lower theoretical stage in a distillation column. An overhead vapor stream is drawn from the distillation column overhead of an upper theoretical stage, and a bottom stream comprising a stream of regenerated glycol is drawn from the distillation column via a bottom outlet configured below the lower theoretical stage. The stream of recovered glycol comprises the regenerated glycol. In addition, a first middle theoretical stage is situated within the distillation column gravitationally above the lower theoretical stage and below the upper theoretical (Continued)

stage. A side stream of liquid water is drawn from the bottom of the upper theoretical stage in the distillation column.

22 Claims, 2 Drawing Sheets

(51) Int. Cl.
| | |
|---|---|
| B01D 53/14 | (2006.01) |
| B01D 53/18 | (2006.01) |
| C10L 3/10 | (2006.01) |
| B01D 53/26 | (2006.01) |
| C07C 31/20 | (2006.01) |

(52) U.S. Cl.
CPC .......... B01D 53/263 (2013.01); C07C 31/202 (2013.01); C10L 3/101 (2013.01); C10L 3/106 (2013.01); C10L 3/107 (2013.01); B01D 2252/2023 (2013.01); C10L 2290/06 (2013.01); C10L 2290/08 (2013.01); C10L 2290/10 (2013.01); C10L 2290/12 (2013.01); C10L 2290/141 (2013.01); C10L 2290/48 (2013.01); C10L 2290/541 (2013.01); C10L 2290/543 (2013.01); C10L 2290/56 (2013.01)

(58) Field of Classification Search
CPC . B01D 53/263; C07C 31/202; C10L 2290/06; C10L 2290/08; C10L 2290/10; C10L 2290/12; C10L 2290/141; C10L 2290/48; C10L 2290/541; C10L 2290/543; C10L 2290/56; C10L 3/101; C10L 3/106; C10L 3/107
See application file for complete search history.

(56) References Cited

U.S. PATENT DOCUMENTS

| | | | |
|---|---|---|---|
| 2005/0022665 A1* | 2/2005 | Baudot | ................ B01D 61/145 95/196 |
| 2007/0134143 A1 | 6/2007 | Carnell | |

OTHER PUBLICATIONS

PCT International Search Report, Application No. PCT/EP2013/062852 dated Jul. 24, 2013.

* cited by examiner

METHOD AND APPARATUS FOR CIRCULATING A GLYCOL STREAM, AND METHOD OF PRODUCING A NATURAL GAS PRODUCT STREAM

CROSS-REFERENCE TO RELATED APPLICATIONS

The present application is a National Stage (§371) application of PCT/EP2013/062852, filed Jun. 20, 2013, which claims the benefit of European Application No. 12173104.6, filed Jun. 22, 2012, and European Application No. 12187663.5, filed Oct. 8, 2012, both of which are incorporated herein by reference in their entirety.

FIELD

The present invention relates to a method and apparatus for recirculation a glycol stream. In other aspects, the present invention relates to a method of producing a natural gas product stream.

BACKGROUND

Recirculation of glycol is often used in a context of transportation of a mixture of hydrocarbons comprising natural gas, water, and dissolved salts in production pipelines from an off-shore located (mineral) hydrocarbon reservoir to a land based or floating top-side facilities for processing the mixture to recover the desired hydrocarbon products. Due to shifting physical conditions during the pipeline transit, there is a problem with formation of hydrates in the fluid mixture of the pipelines threatening to clog the lines. One much applied solution to the problem of hydrate formation is to add, at subsea level, relatively low water content glycol (referred to as lean glycol) into the process fluid which usually is a mixture of hydrocarbons comprising natural gas, water, and dissolved salts, and then extract the glycol as so-called rich glycol from the process fluid at the top-side facilities. The rich glycol has a higher water content than the lean glycol. The glycol often selected for this purpose is mono ethylene glycol (MEG), in which case the lean glycol is referred to as lean MEG and the rich glycol is referred to as rich MEG.

From an operational costs and environmental point of view, the glycol stream should be recirculated. To this end, rich MEG is typically regenerated to form lean MEG and then reused as hydrate inhibiting agent in the production lines. Rich MEG usually contains remains of the hydrocarbons, high water levels, corrosion products, production chemicals and other contaminants originating from the hydrocarbon reservoir.

Typical other contaminants originating from the hydrocarbon reservoir include salts and mercury. Both may be present in the rich MEG stream. The presence of glycol is thought to increase the solubility of elemental mercury in an aqueous phase containing the glycol.

A typical MEG loop is described in Paper No. 10131 of NACE International Corrosion Conference and Expo 2010 titled "Development of a simulator for ethylene glycol loops based on solution thermodynamics and particle formation kinetics", by Marion Seiersten et al., wherein a process stream containing natural gas is conveyed through a pipeline. A MEG stream is injected into a pipeline at a subsea injection point, and mixed with a glycol-containing stream with a production stream in the pipeline. Both are conveyed through the pipeline to receiving facilities, where MEG, formation water and condensed water are separated from the gas and condensate. The rich MEG is heated and depressurized to remove dissolved hydrocarbons. From there the rich MEG is passed via a pre-treatment to a rich MEG storage. A MEG re-concentration system having a boiler to boil off water, and a flash separator for removing salts, and a column for MEG water separation is used to recover the MEG. The recovered MEG is piped back to the subsea injection point via an injection pump after having been stored in a lean MEG storage tank. Water streams are discharged from the boiler and the column.

A concern associated with the typical MEG loop as described above is that the discharged water stream(s) may be contaminated with mercury so much that legislative requirements may preclude discharging of the water into the environment.

SUMMARY

In accordance with a first aspect of the present invention, there is provided a method of circulating a glycol stream, comprising:

conveying a process stream containing natural gas through a pipeline from an upstream location to a downstream location;

injecting a glycol-containing stream into the pipeline at an injection point and conveying the glycol-containing stream with the process stream through the pipeline to the downstream location;

at the downstream location, separating the process stream with the glycol-containing stream into at least an aqueous phase and a natural gas phase, said aqueous phase containing at least a part of the glycol originating from the glycol-containing stream and said natural gas phase containing at least a part of the natural gas from the process stream;

recovering glycol from the aqueous phase to form a stream of recovered glycol, wherein said recovering of glycol from the aqueous phase comprises regenerating glycol by removing water from the glycol in the aqueous phase; and transporting the stream of recovered glycol to the injection point and adding it to the glycol-containing stream being injected;

wherein said regenerating of glycol comprises: feeding the aqueous phase to the top of a lower theoretical stage in a distillation column, drawing a side stream of liquid water from the bottom of an upper theoretical stage in the distillation column, drawing an overhead vapour stream from the distillation column overhead of the upper theoretical stage, and drawing a bottom stream comprising a stream of recovered glycol from the distillation column via a bottom outlet configured below the lower theoretical stage, wherein a first middle theoretical stage is situated within the distillation column gravitationally above the lower theoretical stage and below the upper theoretical stage.

In accordance with a second aspect of the invention there is provided an apparatus for circulating a glycol stream, comprising:

a pipeline extending from an upstream location to a downstream location for conveying a process stream containing natural gas from the upstream location to the downstream location;

an injection point for injecting a glycol-containing stream into the pipeline and into the process stream;

an inlet separation system, at the downstream location, arranged to receive the process stream with the glycol-containing stream and to separate the process stream with the glycol-containing stream into at least an aqueous phase and a natural gas phase, said aqueous phase containing at least a part of the glycol originating from the glycol-containing stream and said natural gas phase containing at least a part of the natural gas from the process stream;

a glycol recovery system comprising an recovery system inlet in fluid communication with the inlet separation system, said glycol recovery system arranged to receive the aqueous phase via the recovery system inlet and to recover glycol from the aqueous phase to form a stream of recovered glycol, said recovery system further comprising a recovery system outlet for discharging the stream of recovered glycol, wherein said glycol recovery system glycol regeneration system; and a glycol injection line fluidly connecting the recovery system outlet with the injection point, said glycol injection line arranged to transport the stream of recovered glycol from the glycol recovery system to the injection point; wherein said glycol regeneration system comprises: a distillation column arranged in a first path between the recovery system inlet and the recovery system outlet, wherein the distillation column comprises a first middle theoretical stage configured gravitationally above a lower theoretical stage and below an upper theoretical stage, all of said first middle theoretical stage and said upper theoretical stage and said lower theoretical stage situated within the distillation column, wherein said distillation column comprises a first feed inlet arranged to receive and feed the aqueous phase from the recovery system inlet to the top of the lower theoretical stage, a side draw-off outlet arranged at the bottom of the upper theoretical stage for drawing a side stream of liquid water from the distillation column, and an overhead vapour outlet arranged overhead of the upper theoretical stage for drawing an overhead vapour stream from the distillation column above the upper theoretical stage, and a bottom outlet configured below the lower theoretical stage for drawing a bottom stream comprising a stream of regenerated glycol from the distillation column, whereby the recovery system outlet is arranged in fluid communication with the bottom outlet to receive the stream of recovered glycol comprising regenerated glycol from the bottom stream.

Moreover, in another aspect of the invention there is provided a method of producing a natural gas product stream, comprising:

conveying a process stream containing natural gas through a pipeline from an upstream location to a downstream location;

injecting a glycol-containing stream into the pipeline at an injection point and conveying the glycol-containing stream through the pipeline to the downstream location;

at the downstream location, separating the process stream with the glycol-containing stream into at least an aqueous phase and a natural gas phase, said aqueous phase containing at least a part of the glycol originating from the glycol-containing stream and said natural gas phase containing at least a part of the natural gas from the process stream;

simultaneously recovering glycol from the aqueous phase to form a stream of recovered glycol and further treating the natural gas phase thereby producing a natural gas product stream;

transporting the stream of recovered glycol to the injection point and adding it to the glycol-containing stream being injected;

wherein said recovering of glycol from the aqueous phase comprises feeding the aqueous phase to the top of a lower theoretical stage in a distillation column, drawing a side stream of liquid water from the bottom of an upper theoretical stage in the distillation column, drawing an overhead vapour stream from the distillation column overhead of the upper theoretical stage, and drawing a bottom stream comprising a stream of recovered glycol from the distillation column via a bottom outlet configured below the lower theoretical stage, wherein a first middle theoretical stage is situated within the distillation column gravitationally above the lower theoretical stage and below the upper theoretical stage.

BRIEF DESCRIPTION OF THE DRAWINGS

The invention will be further illustrated hereinafter by way of example only, and with reference to the non-limiting drawing in which.

DETAILED DESCRIPTION

Figure 1:
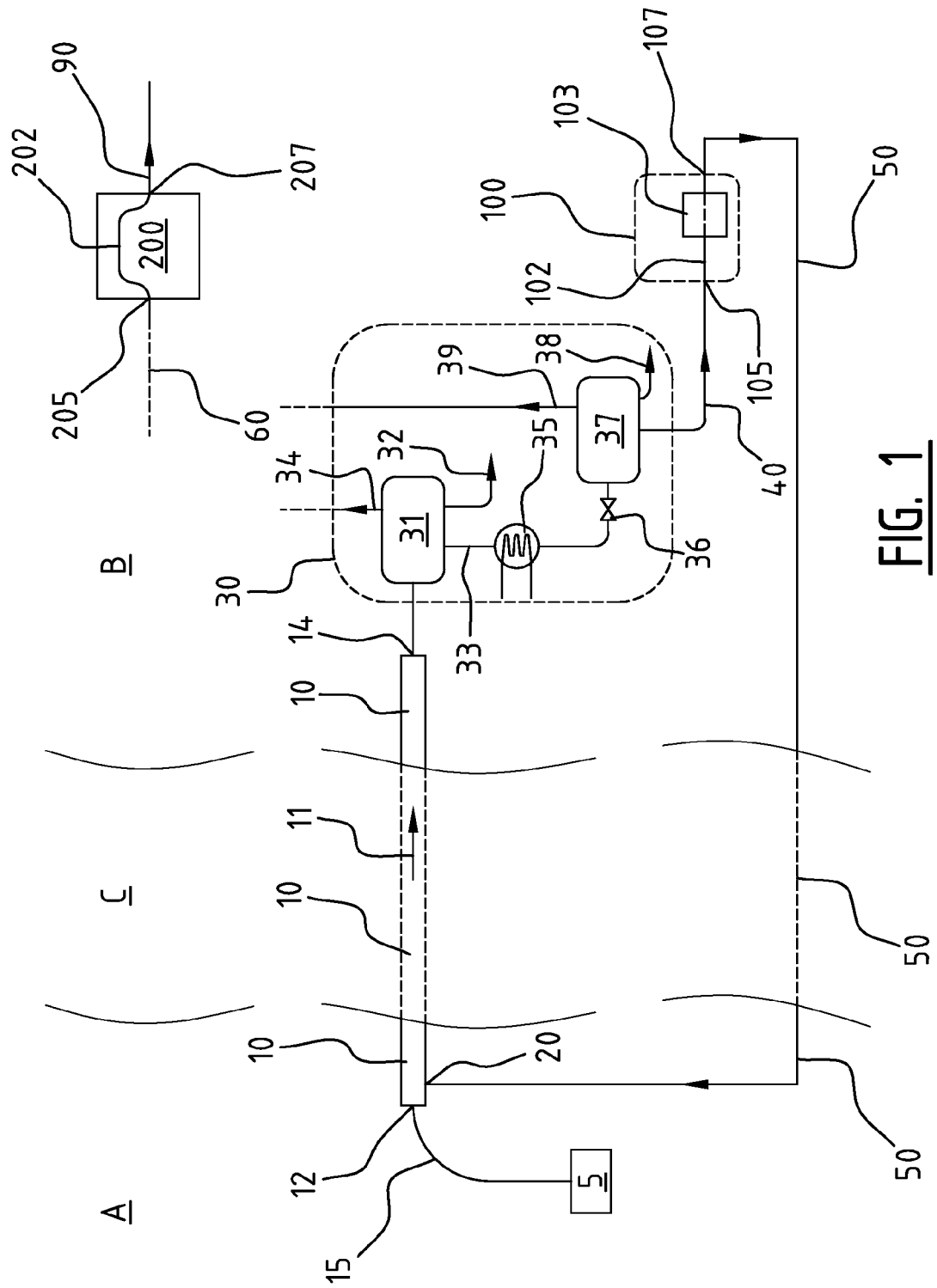
FIG. 1 schematically illustrates a method and apparatus for circulating a glycol stream, involving a glycol recovery system, in a method and apparatus for producing a natural gas product stream.

For the purpose of this description, a single reference number will be assigned to a line as well as a stream carried in that line. Same reference numbers refer to similar components. The person skilled in the art will readily understand that, while the invention is illustrated making reference to one or more a specific combinations of features and measures, many of those features and measures are functionally independent from other features and measures such that they can be equally or similarly applied independently in other embodiments or combinations.

The methods apparatuses described herein involve recovering of glycol from an aqueous phase to form a stream of recovered glycol and a glycol recovery system. The recovering of glycol comprises regenerating of glycol (suitably in a glycol regeneration system) by removing water from the glycol present in the aqueous phase. In the regenerating and/or regeneration system, the aqueous phase is fed to the top of a lower theoretical stage in a distillation column. An overhead vapour stream is drawn from the distillation column overhead of an upper theoretical stage, and a bottom stream comprising a stream of regenerated glycol is drawn from the distillation column via a bottom outlet configured below the lower theoretical stage. In addition, a first middle theoretical stage is situated within the distillation column gravitationally above the lower theoretical stage and below the upper theoretical stage. A side stream of liquid water is drawn from the bottom of the upper theoretical stage in the distillation column.

The regenerated glycol has a lower water content than the aqueous phase being fed into the distillation column. The overhead vapour stream may contain water in vapour phase which is contaminated by volatile contaminants. The side stream of liquid water contains water that is relatively free from volatile contaminants compared to the overhead vapour stream. For instance, in a case where the aqueous phase contains elemental mercury it has been found that the side stream of liquid water may be sufficiently mercury-depleted to be disposed in the environment. Advantageously, no precipitation or flocculation agents are needed, nor equipment for removing the precipitates and flocculates from the aqueous phase as typically needed in methods where mercury is removed by adding a mercury precipitation agent to the aqueous stream.

So the proposed regenerating of glycol during recovery of glycol is capable of both regenerating glycol and produce a stream of liquid water that is that is sufficiently free from glycol and contaminants such as mercury to be disposable into the environment. Advantageously, all can be achieved using a single distillation column.

Certain aspects of the invention relate to a glycol regeneration system and a method of regenerating glycol from an aqueous phase containing glycol. In some of these aspects there is provided a glycol regeneration system comprising a distillation column that comprises a first middle theoretical stage configured gravitationally above a lower theoretical stage and below an upper theoretical stage, all of said first middle theoretical stage and said upper theoretical stage and said lower theoretical stage situated within the distillation column, wherein said distillation column comprises a first feed inlet arranged to receive and feed the aqueous phase to the top of the lower theoretical stage, a side draw-off outlet arranged at the bottom of the upper theoretical stage for drawing a side stream of liquid water from the distillation column, and an overhead vapour outlet arranged overhead of the upper theoretical stage for drawing an overhead vapour stream from the distillation column above the upper theoretical stage, and a bottom outlet configured below the lower theoretical stage for drawing a bottom stream comprising a stream of regenerated glycol from the distillation column. The distillation column and the regeneration system may be arranged in a more-encompassing glycol recovery system, in a first path between a recovery system inlet and a recovery system outlet, whereby the aqueous phase is provided through the recovery system inlet and whereby the recovery system outlet is arranged in fluid communication with the bottom outlet to receive at least the stream of recovered glycol comprising regenerated glycol from the bottom stream.

Suitable examples of glycol include monoethylene glycol (MEG), diethylene glycol (DEG), and triethylene glycol (TEG). Of these, MEG tends to be the most commonly used choice for the purpose of hydrate inhibition in a pipeline.

The presently disclosed methods and apparatuses are not only useful in an offshore environment where plot space is scarce and expensive, but they may also be usefully applied in an onshore environment. In the context of the present specification, the term "subterranean formation" refers to earth formations that can be located offshore or onshore.

Nevertheless, due to the relatively small plot space required to carry out the invention, it is particularly suited for application on an offshore structure, including applications on a floating gas processing structure such as a floating natural gas liquefaction plant.

The term "theoretical stage" as used herein is a term generally used in the art of distillation to denote a zone or stage in which vapour and liquid phases within the distillation column establish a phase equilibrium with each other. A "theoretical stage" is sometimes also referred to as "equilibrium stage", "ideal stage", or "theoretical tray". Any physical device (including trays, packing) that provides good contact between the vapour and liquid phases present in industrial-scale distillation columns constitutes a "plate" or "tray". Since an actual, physical plate is rarely a 100% efficient equilibrium stage, the number of actual plates is more than the required theoretical plates.

Turning now to FIG. 1, there is illustrated apparatus for circulating a glycol stream. A pipeline 10 extends from an upstream location A to a downstream location B, for conveying a process stream 11 containing natural gas from the upstream location A to the downstream location B. The pipeline has an upstream end 12 at the upstream location A, and a downstream end 14 at the downstream location B. Typically, the pipeline 10 fluidly communicates with a hydrocarbon production well 5 via its upstream end 12.

An injection point 20, for injecting a glycol containing stream into the pipeline 10 and into the process stream 11 conveyed therein is provided in the upstream location A. In FIG. 1, the injection point 20 is schematically indicated in the pipeline 10 between its upstream end 12 and its downstream end 14, but this is not a requirement of the invention. It may be located upstream of the upstream end 12, such as in a connection 15 between the hydrocarbon production well 5 and the upstream end 12 of the pipeline 10.

The upstream location A is often situated off-shore, but this is not a main requirement of the invention. However, in many practical applications glycol injection is desired when conveying process streams containing natural gas and water from an off-shore location through an underwater pipeline. The downstream location B can be on shore, as will often be the case, or off-shore on a hydrocarbon processing platform such as on a floating production, storage and offloading unit. Between the upstream location A and the downstream location B is typically a transit zone C, in which essentially the process stream 11 is transported from the upstream location A to the downstream location B. A stream of recovered glycol 50, on the other hand, is transported through the transit zone C from the downstream location B to the upstream location A.

An inlet separation system 30 is provided at the downstream location B. The pipeline 10 is connected to the inlet separator 30 via its downstream end 14. The inlet separation system 30 is arranged to receive the process stream with the injected glycol-containing stream, and to separate the process stream with the glycol-containing stream into at least an aqueous phase 40 and a natural gas phase 60. The aqueous phase 40 contains at least a part of the glycol originating from the glycol containing stream. The natural gas phase does not have to consist purely of natural gas, but it contains at least a part of the natural gas from the process stream.

Inlet separation systems are known to the person of ordinary skill in the art. As a non-limiting example, the inlet separation system 30 of FIG. 1 comprises a high-pressure separator 31 in the form of a three-phase separator, and a low-pressure separator 37. The high-pressure separator 31 is fluidly connected to a hydrocarbon condensate discharge line 32, a high-pressure aqueous phase discharge line 33, and a high-pressure gas phase discharge line 34. The low-pressure separator is connected to the high-pressure aqueous phase discharge line 33 via respectively an optional heater 35 and a pressure reduction valve 36. In the low-pressure separator 37, the high-pressure aqueous phase 33 is separated into an aqueous phase and a low pressure gas phase, and low pressure condensate phase, each of which being discharged from the low-pressure separator 37. To this end, the low-pressure separator is connected to a low-pressure condensate phase discharge line 38, a low-pressure gas phase discharge line 39 and a low pressure aqueous phase discharge line 40.

The aqueous phase 40 from the inlet separation system 30 is drawn from the low-pressure separator 37. One or both of the high-pressure gas phase discharge line 34 and the low-pressure gas phase discharge line 39 may be connected to a natural gas phase line 60 to covey the natural gas phase to a natural gas treatment system 200 as shown by dotted lines. Pressure adjusting equipment, for instance selected from a pressure-reduction valve, an expansion turbine, a compressor, may be inserted as needed to adjust the pressure of the high-pressure gas phase and/or the low-pressure gas phase to obtain a target natural gas treatment pressure. Preferably, the high-pressure gas phase discharge line 34 connects to the natural gas phase line 60 as this makes optimal use of the already available pressure in the pipeline 10.

The high-pressure separator 37 may typically be operated at a pressure of between 40 and 100 bara, such as about 70 bara, and the low-pressure separator may typically be operated at between 10 and 40 bara, such as about 25 bara. Such pressures are examples, and not limiting on the invention.

Also at the downstream location B, a glycol recovery system 100 is provided. The glycol recovery system 100 comprises a recovery system inlet 105 in fluid communication with the inlet separation system 30. The glycol recovery system 100 is arranged to receive the aqueous phase 40 via the recovery system inlet 105, and further to recover glycol from the aqueous phase 40 to form a stream of recovered glycol 50. The recovery system 100 further comprises a recovery system outlet 107, for discharging the stream of recovered glycol 50. A path 102 connects the recovery system outlet 107 with recovery system inlet 105. Units and pieces of equipment of various types may be configured in the path 102 as needed for the recovery of glycol, including a glycol regeneration system 103 wherein water is removed from the glycol, and possibly including one or more of: a pre-treating unit, a salt removal unit, a salt reclamation unit, an acid injection unit, coolers, filters.

The apparatus described so far with reference to FIG. 1, can be employed to circulate a glycol stream from a starting point at the upstream location A via the transit zone C to the downstream location B where it arrives as a rich glycol stream; through a regeneration process wherein the rich glycol stream is regenerated to form a lean glycol stream; and in the form of the lean glycol stream back from the downstream location B via the transit zone C to the upstream location A to the starting point.

Glycol storage means (not shown) may be provided in the glycol circulation loop as desired. Typically, a rich glycol storage tank may be provided to temporarily store the aqueous phase 40 in the downstream location B upstream of the glycol recovery system 100. In addition, a lean glycol storage tank may be provided to temporarily store the recovered glycol stream 50 at the downstream location B prior to conveying it to the upstream location A.

Still referring to FIG. 1, an optional natural gas treatment system 200 may provided, in fluid communication with the inlet separation system 100. This natural gas treatment system 200 is suitably arranged to receive the natural gas phase 60 via a treatment system inlet 205, and to further treat the incoming natural gas phase 60 to form a natural gas product stream 90. The natural gas treatment system 200 may thus further comprise a treatment system outlet 207, for discharging the natural gas product stream 90.

Various types of natural gas treatment systems are known to the person of ordinary skill in the art and the specific selection of the suitable type depends on the demand and requirements. For instance, the natural gas treatment system 200 may comprise one or more of gas treatment units in a natural gas treatment path 202 extending between the treatment system inlet 205 and the treating system outlet 207 as selected from the group consisting of: dew pointing unit, dehydration unit, acid gas removal unit, mercury removal unit, natural gas liquids extraction unit, cooling unit, liquefying unit, nitrogen removal unit, helium removal unit.

During operation, the process stream 11 containing natural gas is conveyed from the hydrocarbon production well 5 via connection 15 through the pipeline 10 from the upstream location A to the downstream location B. The glycol containing stream is injected into the pipeline 10 at the injection point 20, and conveyed with the process stream 11 through the pipeline 10 to the downstream location B. At the downstream location, the process stream 11 with the glycol-containing stream is separated into at least the aqueous phase 40 and the natural gas phase 60. The aqueous phase 40 contains at least a part of the glycol originating from the glycol containing stream. The natural gas phase 60 contains at least a part of the natural gas from the process stream 11. Glycol is recovered from the aqueous phase 40 to form a stream of recovered glycol 50.

The recovered glycol 50 is conveyed in a glycol injection line that fluidly connects the recovery system outlet 107 at the downstream location B with the injection point 20 at the upstream location A. The glycol injection line is arranged to transport the stream of recovered glycol 50 from the glycol recovery system 100 to the injection point 20. Thus, the stream of recovered glycol 50 is transported to the injection point 20 and added to the glycol containing stream being injected.

At the same time, the natural gas phase 60 may be further treated in the optional natural gas treatment system 200, thereby producing the natural gas product stream 90. Such further treating of the natural gas phase 60 may comprise subjecting at least a fraction of the natural gas phase 60 to one or more gas treatment steps selected from the group consisting of: dew pointing, dehydration, acid gas removal, mercury removal, extraction of natural gas liquids, cooling, liquefying, nitrogen removal, helium removal. The various treatment steps and units are known to the person skilled in the art and need no further explanation herein.

Figure 2:
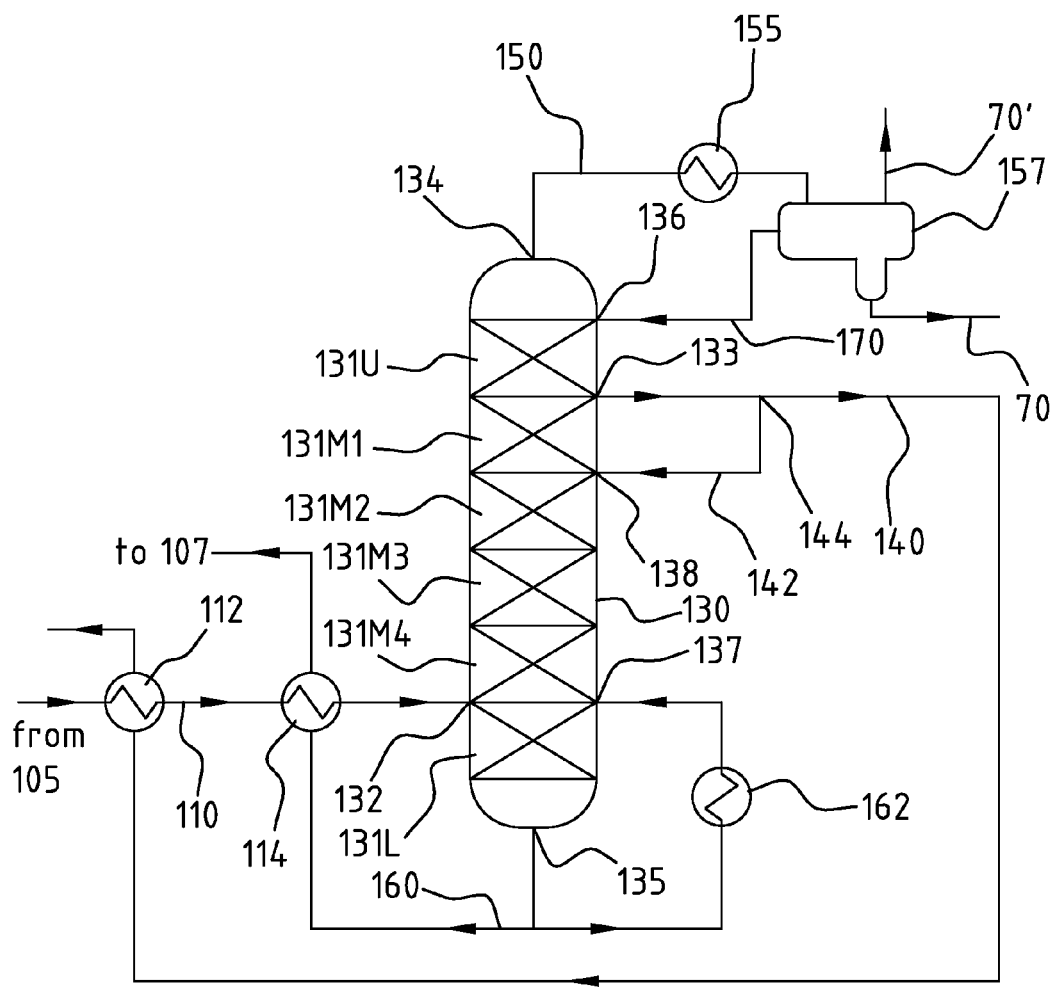
FIG. 2 schematically shows an example for a distillation column forming part of the glycol recovery system.

Turning now to FIG. 2, there is shown a distillation column 130 that forms part of the regeneration system 103 within the glycol recovery system 100. Within the distillation column 130 is configured vapour-liquid contacting equipment, typically in the form of trays or packing (structured packing or unstructured packing), to form a plurality of theoretical stages 131. In the figure, there is indicated an upper theoretical stage 131U, a lower theoretical stage 131L, a first middle theoretical stage 131M1, and optional second (131M2), third (131M3), and fourth (131M4) theoretical stages. The first middle theoretical stage 131M1 is configured gravitationally above the lower theoretical stage 131L and below the upper theoretical stage 131U. If provided, the second middle theoretical stage 131M2 is situated, within the distillation column 130, gravitationally above the lower theoretical stage 131L and below the first middle theoretical stage 131M1. Any number further theoretical stages may be provided between the first middle theoretical stage 131M1 and the upper theoretical stage 131U and/or between the first middle theoretical stage 131M1 and lower theoretical stage 131L. In the example as shown, third and fourth middle theoretical stages are configured between the optional second middle theoretical stage 131M2 and the lower theoretical stage 131U, but this is not a requirement of the invention.

A feed line 110, which communicates with the recovery system inlet 105 via path 102, connects to the distillation column 130 via a first feed inlet 132, preferably at a level corresponding to the top of the lower theoretical stage 131L.

A liquid draw-off tray (not shown) coupled to a side draw-off outlet 133 is arranged at the bottom of the upper theoretical stage 131U, for drawing a side stream of liquid water from the distillation column 130 into a water draw-off line 140. The liquid draw-off tray may be a full liquid draw-off tray or a partial liquid draw-off tray.

An overhead vapour outlet 134 is arranged overhead of the upper theoretical stage 131U, for drawing an overhead vapour stream from the distillation column 130 above the upper theoretical stage 131U into an overhead vapour line 150.

A bottom outlet 135 is configured below the lower theoretical stage 131L, for drawing a bottom stream comprising a stream of regenerated glycol from the distillation column 130. The stream of regenerated glycol generally has a lower content of water than the aqueous phase in feed line 110. The stream of regenerated glycol may be guided into a glycol discharge line 160 for optional further processing to finally become a stream of recovered glycol. The recovery system outlet 107 is arranged in fluid communication with the bottom outlet 135 via the glycol discharge line 160, to receive at least the stream of recovered glycol containing regenerated glycol from the bottom stream.

Suitably, one or more feed heat exchangers are configured in the feed line 110 to pre-heat the aqueous phase before it is fed to the distillation column 130. In the non-liming example as illustrated in FIG. 2, the one or more feed heat exchangers are provided in the form of a first effluent-feed heat exchanger 112 and a second effluent-feed heat exchanger 114, whereby the first effluent feed heat exchanger 112 is configured in feed line 110 between the recovery system inlet 105 and the second effluent-feed heat exchanger 114 and whereby the second effluent-feed heat exchanger 114 is configured between the first effluent-feed heat exchanger 112 and the first feed inlet 132 into the distillation column 130.

In preferred embodiments, an overhead condenser 155 may be provided in the in the overhead vapour line 150 and in fluid communication with the distillation column 130 via the overhead vapour outlet 134. The overhead condenser 155 is arranged to form an overhead condensed phase by at least partly condensing the overhead vapour stream withdrawn from the distillation column 130. The overhead condenser 155 may be provided in the form of an overhead heat exchanger. Suitable types of heat exchangers for this purpose include tube in shell type heat exchangers or pipe in pipe heat exchangers, but preferred is a plate-type heat exchanger, for example a plate-fin heat exchanger and/or a printed circuit heat exchanger, optionally in a cold box.

An overhead separator 157 is fluidly connected to the overhead condenser 155, and arranged to receive the overhead condensed phase produced in the overhead condenser 155. The overhead separator 157 may be connected to a contaminated stream conduit 70 for discharging a contaminated stream. The overhead separator 157 and overhead condenser 155 together form a suitable embodiment of a mercury concentrator, which is configured to form a contaminated stream having an increased concentration of mercury relative to the concentration of mercury in the overhead vapour stream in the overhead vapour line 150. A second contaminated stream (not shown) comprising a relatively high amount of condensed hydrocarbons may also be discharged from the overhead separator 157.

The overhead separator 157 may be provided in the form of a three-phase separator, allowing discharge of an off-gas as a separate stream in addition to the contaminated stream and the residue stream in liquid phase. Alternatively, or in addition to the contaminated stream conduit 70, the contaminated stream may be drawn from the overhead separator 157 in vapour form with the off-gas. This alternative option is indicated in FIG. 2 by means of a contaminated vapour stream outlet line 70'. Such contaminated vapour stream 70' typically contains other vapors besides mercury vapor as well, possibly including lighter hydrocarbons.

The contaminated vapour stream 70' may be passed through a mercury absorption unit known in the art in order to remove mercury from the contaminated vapour stream 70'. It is recommended to apply tracing at the temperature of the overhead condensed phase produced in the overhead condenser 155, to avoid condensing of mercury in the contaminated vapor conduit 70' and flow lines downstream thereof. Once mercury has been removed, the contaminated vapour stream 70' may be disposed of in any suitable way.

For instance, the contaminated vapor stream 70' may be disposed of by flaring and/or direct release into the atmosphere. A drain system may be provided as a last precaution, just before the flare or release nozzle, to ensure that no condensed mercury can be released into the atmosphere. In case of flaring, the drain system may be provided in the flare knock out drum, for instance in the form of an additional boot space provided therein.

Particularly in cases where the natural gas treatment system 200 contains a mercury removal unit, for instance using a mercury absorption unit, the contaminated vapour stream 70' may be added to the natural gas phase 60 to be processed together with the natural gas phase 60. Suitably, this may be done via the high-pressure separator 31 or the low-pressure separator 37. This way, the a mercury removal step in the natural gas treatment system 200 is advantageously used to remove mercury from both the natural gas phase 60 and the contaminated vapour stream 70'.

A residue stream conduit 170 is fluidly connected to the overhead separator 157, for discharging a residue stream from the overhead separator 157. The residue stream conduit 170 is separate from the contaminated stream conduit 70, and the residue stream ideally contains water. The residue conduit 170 is optionally fluidly connected with the distillation column 131 via a top reflux inlet 136. Suitably, the top reflux inlet 136 is configured at the top of the upper theoretical stage 131U. An optional reflux pump (not shown) may be configured in the residue conduit 170 to assist the flow of the residue stream into the distillation column 130.

Instead of, or, preferably, in addition to, the overhead condenser 155 described above, a heater 162 may be provided to add heat to the distillation column 130. The heater may suitably be operated by low pressure steam. Suitably, the heater 162 may be provided in the form of a bottom stream reboiler configured to heat a reboil-part of the bottom stream. The heater 162 may internal or external to the distillation column 130. The particular non-limiting example illustrated in FIG. 2 illustrates the heater 162 external to the distillation column 130 which adds heat to the distillation column 130 by discharging a heated reboil-part of the bottom stream into the distillation column 130 via a reboil inlet 137. Suitably, the reboil inlet is configured below the first middle theoretical stage 131M1, preferably below any of the middle theoretical stages configured inside the distillation column 130. In one embodiment the external heat exchanger may suitably be provided in the form of a vertical shell and tube heat exchanger, but other types of heat exchangers and configurations may be employed instead. For instance, instead of a circulating heat exchanger, of which the vertical shell and tube heat exchanger of FIG. 2 is an example, a kettle may be used. Preferably, the heater 162 is arranged to add heat to the distillation column 130 below the first middle theoretical stage 131M1.

With the heater 162, the distillation column 130 may essentially function as a boiler to boil-off water from glycol and at the same time as a steam stripper to strip contaminants from the water before it is drawn off from the distillation column 130 in the water draw-off line 140. To further facilitate the distillation efficiency and allow control over the amount of glycol in the liquid water of the side stream, an optional side stream return line 142 may connected to the side draw-off outlet 133, for instance via a T-junction 144 in the water draw-off line 140, and to a side reflux inlet 138, to return part of the side stream of liquid water to the distillation column 130 as a side reflux stream. An optional side reflux pump (not shown) may be configured in the optional side stream return line 142. The side reflux inlet 138 is configured in the distillation column 130 at a level below the bottom of the upper theoretical stage 131U. Alternatively to the T-junction and side reflux inlet 138, a partial liquid draw-off tray may be employed in the distillation column 130.

If the distillation column 130 further comprises a second middle theoretical stage 131M2 above the lower theoretical stage 131L and below the first middle theoretical stage 131M1, the side reflux inlet 138 is suitably configured at the top of the second middle theoretical stage 131M2, below the first middle theoretical stage 131M1.

The water draw-off line 140 may further be connected to a disposal zone. In a preferred embodiment, the water draw-off line 140 may pass through the first effluent-feed heat exchanger 112. The glycol discharge line 160 is connected to the recovery system outlet 107 and discharged from the glycol recovery system 100 via the recovery system outlet 107. In a further preferred embodiment, in addition to or instead of the water draw-off line 140 passing through the first effluent-feed heat exchanger 112 the glycol discharge line may pass through the second effluent-feed heat exchanger 114, which is arranged between the bottom outlet 135 and the glycol recovery system outlet 107.

Still with reference to FIG. 2, during operation the recovering of glycol from the aqueous phase comprises feeding the aqueous phase to the top of the lower theoretical stage 131L in the distillation column 130. The pressure in the distillation column may be in the range of from 1.1 bara to 10 bara, preferably from 1.1 bara to 5 bara, more preferably from 1.1 bara to 2.7 bara. The lower pressures are preferred, to allow operating the distillation column 130 at temperatures below degradation temperature of the glycol being recovered, which facilitates the possibility to reuse the recovered glycol.

An overhead vapour stream is drawn from the distillation column 130 via the overhead vapour outlet 134, while the bottom stream comprising a stream of regenerated glycol is drawn from the distillation column 130 via the bottom outlet 135. Before discharging the regenerated glycol from the glycol recovery system 100 in the form of recovered glycol via the recovery system outlet 107, excess heat vested in the regenerated glycol may be at used to heat up the aqueous phase in feed line 110, for instance by passing the regenerated glycol through the second effluent-feed heat exchanger 114.

A side stream of liquid water is drawn from the bottom of the upper theoretical stage 131U in the distillation column 130 by the water draw-off line 140. The liquid water may be sufficiently clean to be disposed of by discharging it into the environment. Prior to disposal, any excess heat vested in the liquid water may be used to heat up the aqueous phase in feed line 110, for instance by passing the liquid water through the first effluent-feed heat exchanger 112.

If the overhead condenser 155 is provided, the overhead vapour stream may be at least partially, or fully, condensed in the overhead condenser 155 to form an overhead condensed phase. During condensation heat may be extracted by cooling against a stream drawn from the ambient, such as an ambient air stream, or preferably a water stream preferably drawn from sea or a lake. The temperature of the overhead condensed phase as it is discharged from the overhead condenser 155 may be in the range of from 5° C. to 70° C., preferably from 5° C. to 50° C., and preferably below 35° C. to minimize partitioning of elemental mercury in the contaminated vapor stream 70'. Temperatures below 35° C. can usually be achieved using cooling against ambient, particularly against ambient air or ambient (sea) water.

The overhead condensed phase is then fed to the optional overhead separator 157, and a contaminated stream comprising a contaminant is removed from the overhead separator 157. In addition, a residue stream is drawn from the overhead separator 157, via the residue stream conduit 170.

The contaminated stream may be removed from the overhead separator 157 in an all-liquid phase via the contaminated stream conduit 70. The contaminated stream may be removed continuously or in batches at intervals. In particular if the amount of liquid generated is relatively low, the contaminated stream may be accumulated in a boot space and periodically drained for instance during maintenance turn arounds.

Alternatively, the contaminated stream may be drawn from the overhead separator 157 in the vapour form via contaminated vapour stream outlet line 70'. The partitioning of the contaminant over the contaminated stream 70 in liquid phase and contaminated vapor stream 70' can be influenced by controlling the temperature of the overhead condensed phase being discharged from the overhead condenser 155.

The residue stream is separate from the contaminated stream, and contains less of the contaminant than the contaminated stream in contaminated stream conduit 70. The residue stream 170 preferably comprises water; preferably it consists for at least 90% of water. Suitably at least a part of the residue stream, preferably all of the residue stream, is returned to the distillation column 130 and fed into the distillation column 130 as a reflux stream. A suitable place for feeding the reflux stream into the distillation column 130 is at the top of the upper theoretical stage 131U.

Instead of the reflux stream, or, preferably, in addition to the reflux stream described in the preceding paragraph, a part of the side stream of liquid water may be returned to the distillation column 130 as a side reflux stream. Suitably, such side reflux stream is fed into the distillation column 130 via the side reflux inlet 138. Suitably, such side reflux stream is fed into the distillation column 130 at a level in the distillation column 130 below the bottom of the upper theoretical stage 131U. If the distillation column 130 further comprises a second middle theoretical stage 131M2 gravitationally above the lower theoretical stage 131L and below the first middle theoretical stage 131M1, the side reflux stream may preferably be fed into the distillation column 130 at the top of the second middle theoretical stage 131M2. The side reflux stream helps to control the amount of glycol that is removed from the distillation column 130 with the side stream of liquid water in water draw-off line 140.

Preferably, heat is added to the distillation column 130 below the first middle theoretical stage 131M1. This helps to boil off water from the glycol. Moreover, if the aqueous phase contains a relatively volatile contaminant, such as dissolved elemental mercury, adding heat helps to bring the volatile contaminant into the vapour phase so that it can eventually be removed with the overhead vapour via overhead vapour line 150. The adding of heat may comprise heating at least part of the bottom stream thereby providing a reboiled part of the bottom stream and feeding the reboiled part of the bottom stream into the distillation column 130 below the first middle theoretical stage 131M1. Preferably, the reboiled part of the bottom stream contains vapour. It may suitably consist of a mixture of liquid and vapour. The temperature of the reboiled part of the bottom stream may be between 110° C. and 230° C., preferably between 110° C. and 180° C., more preferably between 110° C. and 165° C., most preferably between 110° C. and 150° C. In case the glycol is in the form of MEG, a temperature range of 110° C. and 165° C., preferably between 110° C. and 150° C. is recommended to ensure that the MEG is not heated to above its degradation temperature.

A common contaminant in many cases in the field of natural gas production and processing is likely to be formed by elemental mercury, because the presence glycol in the aqueous phase is thought to increase the solubility of elemental mercury in the aqueous phase. In such cases, the contaminated stream essentially consists of, preferably consists of, liquid elemental mercury.

The glycol regeneration in the above described glycol recovery methods and apparatuses is capable of producing a side stream of liquid water within the specification of less than 10 ppbwt (parts per billion by weight) of mercury and less than 1000 ppbwt glycol.

A model simulation has been performed of the regenerating of glycol in the above described methods and apparatuses, with removal of elemental mercury, using the distillation column configuration as shown in FIG. 2. The number of theoretical stages was set to six, excluding the theoretical stages at the overhead condenser 155 and heater 162. The overhead separator 157 is a three-phase separator, and used as an accumulator to separate liquid mercury from the residue stream (mainly water) and the off-gas. A reflux stream consisting of all of the residue stream in residue stream conduit 170 from the overhead separator 157 is fed into the distillation column 130 via the top reflux inlet 136 configured at the top of the upper theoretical stage 131U. The produced water is drawn from the side draw-off outlet 133 arranged at the bottom of the upper theoretical stage 131U, and is partially returned to the theoretical stage below as side reflux. The glycol stream is drawn from the reboiler circulation flow before the heater 162.

In the simulation, an aqueous phase in feed line 110 was fed at bubble point (at a pressure of 150 kPa and 106.6° C.) into the distillation column 130 above the lower theoretical stage 131L (the sixth theoretical stage, in this example) at a rate of 18.81 kg/s. The aqueous phase contains 53 wt. % of MEG and 51 ppbwt of elemental mercury. The reboiled part of the bottom stream was kept at 138.8° C. (above 110° C. and below 140° C.). With a circulation rate of about 240 kg/s, the duty in the heater 162 was 18.68 MW. The reboiled part of the bottom stream fed back into the distillation column 130 consisted of a mixed phase of about 96.5 wt. % liquid and about 3.5 wt. % vapour. The overhead condenser 155 duty was 16.96 MW and the outlet temperature of the overhead condensed phase leaving the overhead condenser 155 was set to 30° C. A flow of 12.45 kg/s of lean MEG having 80 wt. % MEG purity was removed from the distillation process via glycol discharge line 160. The flow rate of the side reflux stream was 1.4 kg/s.

The mercury was distributed as follows over the removed streams: 54% in the contaminated stream conduit 70; 17% in the contaminated vapour stream outlet line 70'; 29% in the lean MEG in glycol discharge line 160; and 0% in the liquid water in the water draw-off line 140; the sum being 100% of the mercury. It can be seen that the method and apparatus are effective to direct mercury in streams other than the liquid water side stream.

The amount of mercury in the side stream of liquid water was 0.0117 ppbwt and the amount of MEG was 519 ppbwt.

The amount of MEG in the stream of liquid water can be regulated independently, or at least practically independently, from the amount of mercury in the stream of liquid water by regulating the flow rate of the side reflux stream. This has been demonstrated by lowering the flow rate of rate of the side reflux stream to 1.185 kg/s leaving the remaining parameters essentially unchanged. The model simulation resulted in an amount of 998 ppbwt of MEG whereas the amount of (elemental) mercury came out as 0.0118 ppbwt, which within the computational error of the simulation is the same as with the 1.4 kg/s flow rate of the side reflux stream.

The partitioning of mercury between the contaminated stream 70 and the contaminated vapour stream 70' can be influenced by regulating the temperature of temperature of the overhead condensed phase leaving the overhead condenser 155 ("condenser temperature"). Table 1 below shows simulation results of the distribution of mercury over the contaminated stream conduit 70; the contaminated vapor stream outlet line 70'; the glycol discharge line 160; and the water draw-off line 140.

TABLE 1

| Temperature | 30° C. | 40° C. | 60° C. |
|---|---|---|---|
| Liquid Hg (line 70) | 54% | 24% | 0% |
| Vapour Hg (line 70') | 17% | 37% | 62% |
| Lean MEG (line 160) | 29% | 39% | 38% |
| liquid water (line 140) | 0% (0.0118 ppbwt) | 0% (0.0118 ppbwt) | 0% (0.0118 ppbwt) |
| sum | 100% | 100% | 100% |

As can be seen, the concentration of mercury in the liquid water is unaltered and remains negligible at least for condenser temperatures between 30° C. and 60° C. No liquid mercury can be drawn from the overhead separator 157 when the condenser temperature rises above 50° C. Thus by setting the condenser temperature the amount of mercury that is allowed to partition into the contaminated vapour stream 70' can be controlled to meet an acceptable level.

This ends the description of the model simulation.

The methods and apparatuses described above can be used in a method of producing a natural gas product stream. Such method would comprise:

conveying the process stream 11 containing natural gas through the pipeline 10 from the upstream location A to the downstream location B;

injecting the glycol containing stream into the pipeline 10 at the injection point 20 and conveying the glycol containing stream through the pipeline to the downstream location B;

at the downstream location B, separating the process stream 11 with the glycol-containing stream into at least the aqueous phase 40 and the natural gas phase 60.

Simultaneously with the recovering of glycol from the aqueous phase 40 to form the stream of recovered glycol 50 as described hereinabove, the natural gas phase 60 is further treated thereby producing the natural gas product stream 90. As described hereinabove, the stream of recovered glycol 50 is transported to the injection point 20 and added to the glycol containing stream being injected.

The further treating of the natural gas phase 60 may comprise subjecting at least a fraction of the natural gas phase 60 to one or more gas treatment steps selected from the group consisting of: dew pointing, dehydration, acid gas removal, mercury removal, extraction of natural gas liquids, cooling, liquefying, nitrogen removal, helium removal.

If the natural gas treatment system 200 comprises at least a liquefaction unit in its natural gas treatment path 202 and/or the further treating of the natural gas phase 60 comprises at least a step of liquefying, the natural gas product stream can be produced in the form of a liquefied natural gas stream, which may be stored at cryogenic temperature (typically below about −160° C. at near atmospheric conditions of 1.2 bara or less) and shipped in bulk form by tankers.

The natural gas treatment system 200 together with the glycol recovery system and optionally together with the inlet separation system may all be provided on a single floating platform for instance on a floating vessel comprising one or more storage tanks. The one or more storage tanks may be provided downstream of the natural gas treatment system 200, and arranged to receive and store the natural gas product stream until it can be offloaded.

In the methods and apparatuses described above, any embodiments allowing for smaller equipment are particularly advantageous if the downstream location B is off-shore, since off-shore space for processing equipment is relatively scarce and comes at a high added cost.

The person skilled in the art will understand that the present invention can be carried out in many various ways without departing from the scope of the appended claims.

The invention claimed is:

1. A method of circulating a glycol stream, comprising:
conveying a process stream containing natural gas through a pipeline from an upstream location to a downstream location;
injecting a glycol-containing stream into the pipeline at an injection point and conveying the glycol-containing stream with the process stream through the pipeline to the downstream location;
at the downstream location, separating the process stream with the glycol-containing stream into at least an aqueous phase and a natural gas phase, said aqueous phase containing at least a part of the glycol originating from the glycol-containing stream and said natural gas phase containing at least a part of the natural gas from the process stream;
recovering glycol from the aqueous phase to form a stream of recovered glycol, wherein said recovering of glycol from the aqueous phase comprises regenerating glycol by removing water from the glycol in the aqueous phase; and
transporting the stream of recovered glycol to the injection point and adding it to the glycol-containing stream being injected;
wherein said regenerating of glycol comprises:
feeding the aqueous phase to a top of a lower theoretical stage in a distillation column,
drawing a side stream of liquid water from a bottom of an upper theoretical stage in the distillation column,
drawing an overhead vapour stream from the distillation column overhead of the upper theoretical stage, and
drawing a bottom stream comprising a stream of recovered glycol from the distillation column via a bottom outlet configured below the lower theoretical stage,
wherein a first middle theoretical stage is situated within the distillation column gravitationally above the lower theoretical stage and below the upper theoretical stage.

2. The method of claim 1, further comprising adding heat to the distillation column below the first middle theoretical stage.

3. The method of claim 2, wherein said adding of heat comprises heating at least part of the bottom stream thereby providing a reboiled part of the bottom stream and feeding the reboiled part of the bottom stream into the distillation column below the first middle theoretical stage.

4. The method of claim 1, wherein a part of the side stream of liquid water is returned to the distillation column as a side reflux stream to a level in the distillation column below the bottom of the upper theoretical stage.

5. The method of claim 4, wherein the distillation column further comprises a second middle theoretical stage situated within the distillation column gravitationally above the lower theoretical stage and below the first middle theoretical stage, wherein the side reflux stream is fed into the distillation column at the top of the second middle theoretical stage.

6. The method of claim 1, further comprising:
at least partially condensing the overhead vapour stream to form an overhead condensed phase;
feeding the overhead condensed phase to an overhead separator;
removing a contaminated stream comprising a contaminant from the overhead separator;
drawing a residue stream from the overhead separator which residue stream is separate from the contaminated stream and contains less of the contaminant than the contaminated stream.

7. The method of claim 6, wherein the contaminated stream is removed from the overhead separator in vaporous form and passed through a mercury removal step.

8. The method of claim 6, wherein the overhead condensed phase is cooled against ambient.

9. The method of claim 6, wherein the overhead condensed phase has a temperature in the range of from 5° C. to 35° C.

10. The method of claim 6, further comprising:
feeding at least a part of the residue stream to the distillation column as a reflux stream.

11. The method of claim 10, wherein the at least part of the residue stream is fed to the distillation column at the top of the upper theoretical stage.

12. The method of claim 6, wherein the contaminant is elemental mercury.

13. The method of claim 12, wherein the contaminated stream essentially consists of liquid elemental mercury.

14. The method of claim 6, wherein the overhead condensed phase has a temperature in the range of from 5° C. to 70° C.

15. The method of claim 6, wherein the overhead condensed phase has a temperature in the range of from 5° C. to 50° C., and preferably below 35° C.

16. An apparatus for circulating a glycol stream, comprising:
a pipeline extending from an upstream location to a downstream location for conveying a process stream containing natural gas from the upstream location to the downstream location;
an injection point for injecting a glycol-containing stream into the pipeline and into the process stream;
an inlet separation system, at the downstream location, arranged to receive the process stream with the glycol-containing stream and to separate the process stream with the glycol-containing stream into at least an aqueous phase and a natural gas phase, said aqueous phase containing at least a part of the glycol originating from the glycol-containing stream and said natural gas phase containing at least a part of the natural gas from the process stream;

a glycol recovery system comprising a recovery system inlet in fluid communication with the inlet separation system, said glycol recovery system arranged to receive the aqueous phase via the recovery system inlet and to recover glycol from the aqueous phase to form a stream of recovered glycol, said recovery system further comprising a recovery system outlet for discharging the stream of recovered glycol, wherein said glycol recovery system comprises a glycol regeneration system for removing water from the glycol in the aqueous phase; and a glycol injection line fluidly connecting the recovery system outlet with the injection point, said glycol injection line arranged to transport the stream of recovered glycol from the glycol recovery system to the injection point;

wherein said glycol regeneration system comprises: a distillation column arranged in a first path between the recovery system inlet and the recovery system outlet, wherein the distillation column comprises a first middle theoretical stage configured gravitationally above a lower theoretical stage and below an upper theoretical stage, all of said first middle theoretical stage and said upper theoretical stage and said lower theoretical stage situated within the distillation column, wherein said distillation column comprises a first feed inlet arranged to receive and feed the aqueous phase from the recovery system inlet to a top of the lower theoretical stage, a side draw-off outlet arranged at a bottom of the upper theoretical stage for drawing a side stream of liquid water from the distillation column, and an overhead vapour outlet arranged overhead of the upper theoretical stage for drawing an overhead vapour stream from the distillation column above the upper theoretical stage, and a bottom outlet configured below the lower theoretical stage for drawing a bottom stream comprising a stream of regenerated glycol from the distillation column, whereby the recovery system outlet is arranged in fluid communication with the bottom outlet to receive the stream of recovered glycol comprising regenerated glycol from the bottom stream.

17. The apparatus of claim 16, further comprising a heater, preferably in the form of a bottom stream reboiler, wherein said heater is arranged to add heat to the distillation column below the first middle theoretical stage.

18. The apparatus of claim 16, further comprising a side stream return line connected to the side draw-off outlet to return part of the side stream of liquid water to the distillation column as a side reflux stream to a level in the distillation column below the bottom of the upper theoretical stage, preferably wherein the distillation column further comprises a second middle theoretical stage situated within the distillation column gravitationally above the lower theoretical stage and below the first middle theoretical stage, wherein the side stream return line feeds into the distillation column at the top of the second middle theoretical stage.

19. The apparatus of claim 16, further comprising:

an overhead condenser in fluid communication with the distillation column via the overhead vapour outlet and arranged to form an overhead condensed phase by at least partly condensing the overhead vapour stream withdrawn from the distillation column;

an overhead separator fluidly connected to the overhead condenser and arranged to receive the overhead condensed phase, said overhead separator being connected to a contaminated stream conduit for discharging a contaminated stream;

a residue stream conduit fluidly connected to the overhead separator for discharging a residue stream from the overhead separator, which residue stream conduit is separate from the contaminated stream conduit.

20. The apparatus of claim 19, wherein said residue stream conduit is fluidly connected with the distillation column, preferably at the top of the upper theoretical stage, to feed at least a part of the residue stream to the distillation column as a reflux stream.

21. A method of producing a natural gas product stream, comprising:

conveying a process stream containing natural gas through a pipeline from an upstream location to a downstream location;

injecting a glycol-containing stream into the pipeline at an injection point and conveying the glycol-containing stream through the pipeline to the downstream location;

at the downstream location, separating the process stream with the glycol-containing stream into at least an aqueous phase and a natural gas phase, said aqueous phase containing at least a part of the glycol originating from the glycol-containing stream and said natural gas phase containing at least a part of the natural gas from the process stream;

simultaneously recovering glycol from the aqueous phase to form a stream of recovered glycol and further treating the natural gas phase thereby producing a natural gas product stream;

transporting the stream of recovered glycol to the injection point and adding it to the glycol-containing stream being injected;

wherein said recovering of glycol from the aqueous phase comprises feeding the aqueous phase to a top of a lower theoretical stage in a distillation column, drawing a side stream of liquid water from a bottom of an upper theoretical stage in the distillation column, drawing an overhead vapour stream from the distillation column overhead of the upper theoretical stage, and drawing a bottom stream comprising a stream of recovered glycol from the distillation column via a bottom outlet configured below the lower theoretical stage, wherein a first middle theoretical stage is situated within the distillation column gravitationally above the lower theoretical stage and below the upper theoretical stage.

22. The method of claim 21, wherein said further treating of said natural gas phase comprises subjecting at least a fraction of the natural gas phase to one or more gas treatment steps selected from the group consisting of: dew pointing, dehydration, acid gas removal, mercury removal, extraction of natural gas liquids, cooling, liquefying, nitrogen removal, helium removal.

* * * * *